United States Patent
Ludin et al.

(10) Patent No.: US 6,193,683 B1
(45) Date of Patent: Feb. 27, 2001

(54) CLOSED LOOP TEMPERATURE CONTROLLED PHACOEMULSIFICATION SYSTEM TO PREVENT CORNEAL BURNS

(75) Inventors: Lev Ludin, Chestnut Hill, MA (US); Edward R. Zaleski, Santa Ana, CA (US)

(73) Assignee: Allergan, Irvine, CA (US)

( * ) Notice: Subject to any disclaimer, the term of this patent is extended or adjusted under 35 U.S.C. 154(b) by 0 days.

(21) Appl. No.: 09/373,462

(22) Filed: Jul. 28, 1999

(51) Int. Cl.[7] .................................................. A61B 17/20
(52) U.S. Cl. .............................. 604/22; 604/28; 604/31; 606/107
(58) Field of Search ............................. 606/107; 604/22, 604/28, 31; 601/2

(56) References Cited

U.S. PATENT DOCUMENTS

| | | |
|---|---|---|
| 4,328,803 * | 5/1982 | Pape . |
| 5,616,120 * | 4/1997 | Andrew et al. . |
| 5,700,240 * | 12/1997 | Barwick, Jr. et al. . |
| 5,766,146 * | 6/1998 | Barwick, Jr. et al. . |
| 5,830,176 * | 11/1998 | MacKool . |
| 5,944,687 * | 8/1999 | Benett et al. . |
| 6,001,069 * | 12/1999 | Tachibana et al. . |

* cited by examiner

Primary Examiner—Mark Bockelman
(74) Attorney, Agent, or Firm—Walter A. Hackler

(57) ABSTRACT

Phacoemulsification apparatus includes a handpiece having a needle and electrical apparatus for ultrasonically vibrating the needle. A power source provides electrical power to the handpiece electrical apparatus and irrigation fluid is provided to the handpiece needle and aspirated therefrom during phacoemulsification. Temperature sensors are provided for determining the temperature of the handpiece needle and a control unit is provided for varying a power level provided the handpiece electrical apparatus and the power source in response to the needle temperature. Alternatively, the control unit functions to vary either irrigation fluid flow or aspiration fluid flow from the handpiece in response to the needle temperature.

12 Claims, 3 Drawing Sheets

CLOSED LOOP TEMPERATURE CONTROLLED PHACOEMULSIFICATION SYSTEM TO PREVENT CORNEAL BURNS

The present invention is generally directed to apparatus and a method for controlling power to a phacoemulsification handpiece needle as well as for controlling the flow of fluid to and from the handpiece needle during phacoemulsification.

More specifically, the present invention relates to the control of power and fluid flow to a phacoemulsification handpiece based on a determination of handpiece needle temperature.

Phacoemulsification systems typically include a handpiece having an ultrasonically vibrated hollow needle and an electronic control therefor.

As is well known in the art, the phacoemulsification handpiece is interconnected with a control console by an electric cable for powering and controlling the piezoelectric transducer and tubing for providing irrigation fluid to the handpiece and withdrawing aspiration fluid from an eye through the handpiece.

The hollow needle of the handpiece is typically driven or excited along its longitudinal axis by the piezoelectric effect in crystals created by an AC voltage applied thereto. The motion of the driven crystal is amplified by a mechanically resonant system within the handpiece, such that the motion of the needle connected thereto is directly dependent upon the frequency at which the crystal is driven with a maximum motion occurring at a resonant frequency.

Vibration of the needle also causes heating thereof which can be detrimental to corneal tissue. In fact, overheating of the needle tip during phacoemulsification procedures can cause non-recoverable corneal burns. Accordingly, it is beneficial to the ophthalmologist performing the phacoemulsification procedure to be able to prevent these occurrences.

In addition, overheating of the needle may increase bubble formation at the tip of the needle which may interfere with the phacoemulsification procedure.

The present invention overcomes these problems by providing control of the phacoemulsification apparatus through closed loop temperature control.

SUMMARY OF THE INVENTION

The phacoemulsification apparatus in accordance with the present invention generally includes the phacoemulsification handpiece having a needle and electrical means for ultrasonically vibrating the needle. The power source means is included for providing electrical power to the handpiece electrical means. Also included are means for providing irrigation fluid to the handpiece needle and means for aspirating the fluid from the handpiece needle.

Importantly, means for sensing a temperature of the handpiece needle and control means are provided for varying a power level provided to the handpiece and electrical means from the power source means in response to the needle temperature.

More particularly, the control means may vary a pulse duty cycle of the power provided to the handpiece needle by the power source means in response to the sensed needle temperature.

Alternatively, the control means may vary the irrigation fluid rate to the handpiece in response to the needle temperature or vary an aspiration fluid rate from the handpiece needle in response to the needle temperature.

More particularly, the apparatus includes an irrigation sleeve surrounding the handpiece needle and the means for sensing needle temperature comprises at least one temperature sensor disposed along the irrigation sleeve. The temperature sensor may be installed next to the junction of the handpiece needle and a handpiece horn either inside or outside of a handpiece shell.

Alternatively, the means for sensing the needle temperature may include a plurality of spaced apart temperature and sensors which may be insert molded into the irrigation sleeve. A harness means may be provided for interconnecting each of the temperature sensors to the control means.

The present invention also provides for a method for operating a phacoemulsification system. Such a system includes a phacoemulsification handpiece needle and an ultrasonic power source, a vacuum source, a source of irrigating fluid and a control unit for controlling ultrasonic power provided to the handpiece needle and the aspiration of irrigation fluid from the handpiece needle. The method includes the steps of placing the handpiece needle in an operative relationship with an eye for a phacoemulsification procedure and thereafter supplying irrigation fluid from the irrigation fluid source to and through the handpiece needle and into the eye.

The steps in accordance with the present invention further include providing ultrasonic power from the ultrasonic power source to the handpiece needle for performing the phacoemulsification procedure and applying vacuum from the vacuum source to the handpiece needle and thereby aspirating the irrigating fluid from the eye through the handpiece at a selected rate. The temperature of the handpiece needle is sensed and in response thereto, the method in accordance with the present invention, variably controls, in response to the needle temperature, the ultrasonic power being provided to the handpiece needle.

Alternatively, in response to the needle temperature, the irrigation fluid flow and/or aspiration of the irrigation fluid from the handpiece needle may be controlled.

BRIEF DESCRIPTION OF THE DRAWINGS

The advantages and features of the present invention will be better understood by the following description when considered in conjunction with the accompanying drawings in which.

DETAILED DESCRIPTION OF THE DRAWINGS

Figure 1:
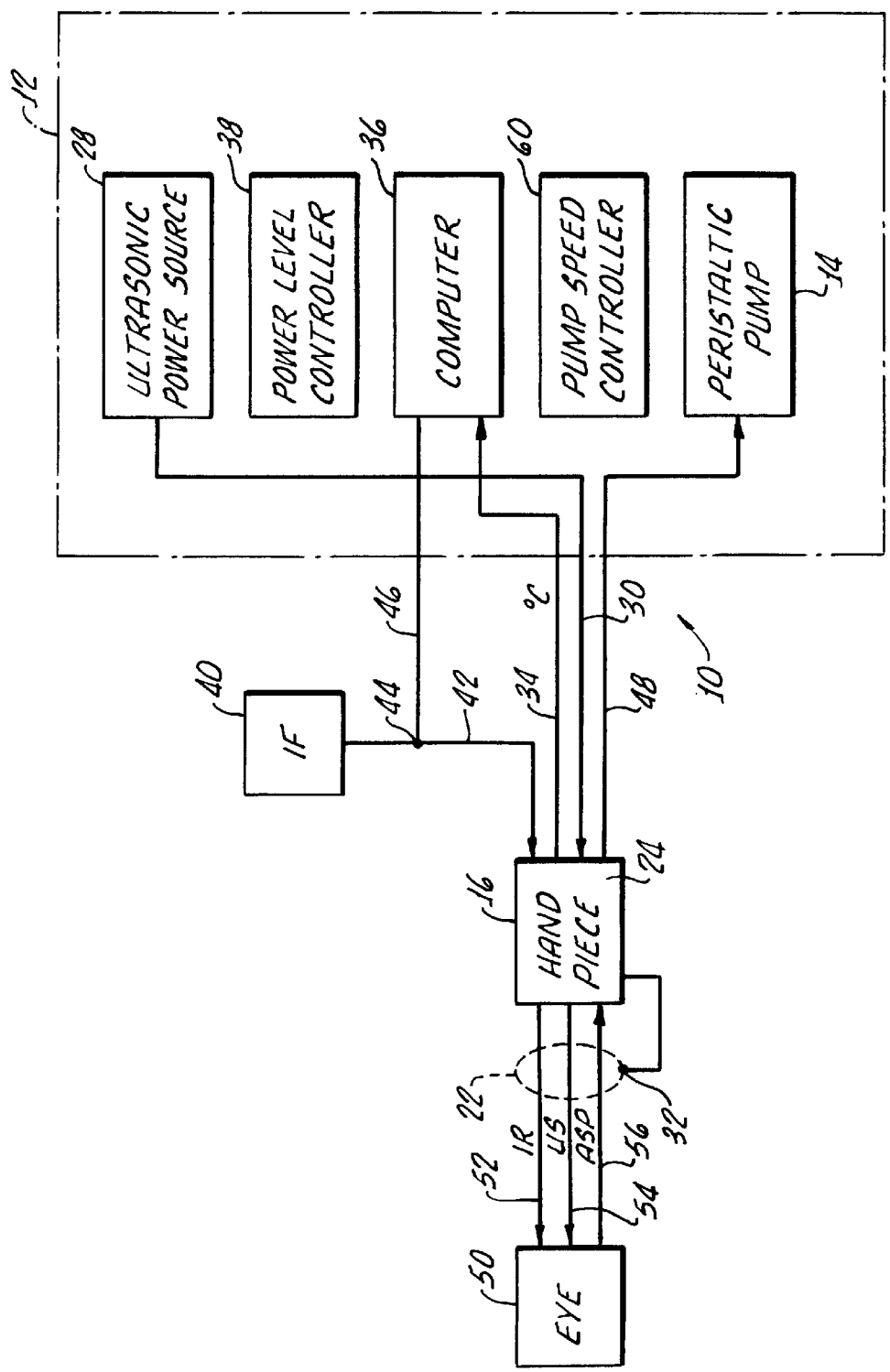
FIG. 1 is a functional diagram of the phacoemulsification apparatus in accordance with the present invention.

With reference to FIG. 1, there is shown in functional block diagram form, a phacoemulsification system indicated generally by the reference numeral 10. The system 10 includes a control unit, or means, 12, indicated by the dashed lines in FIG. 1, which includes a variable speed peristaltic pump 14 which provides a vacuum source to the handpiece 16 through line 18. The handpiece 16 includes a needle assembly represented by the dashed line 22 in FIG. 1 and electrical means 24, also shown in dashed line, for ultrasonically vibrating a needle 26, see FIG. 2.

An ultrasonic power source 28 provides electrical power to the handpiece electrical means 24 through a line 30. Means indicated at 32 in FIG. 1 are provided for sensing the temperature of the handpiece needle 26, as will be hereinafter described in greater detail. A signal corresponding to the needle 26 temperature is provided through a line 34 to a computer 36 which, in combination with a power level controller, provides control means for varying a power level provided to the handpiece electrical means 24 in response to the needle 26 temperature.

A source 40 of irrigation fluid is provided to the handpiece needle 26 through an irrigation line 42 and valve 44 which is controlled by a line 46 interconnecting the valve 46 to the computer 36. Accordingly, the computer 36 provides a control means for varying the irrigation fluid rate in response to the needle temperature. The irrigation fluid is circulated into the eye 50 by the handpiece needle 26 as indicated by the line 52. A representation of ultrasound is also provided in FIG. 1 by the arrow 54, as it is coupled to the eye by the handpiece needle 26.

Aspiration of fluids from the eye by the needle 26 is indicated by the line 56 as conveyed to the peristaltic pump 14 through the line 18, the peristaltic pump, in turn, being controlled by a controller 60 which, in turn, is controlled by the computer 36 in response to the needle temperature.

Figure 2:
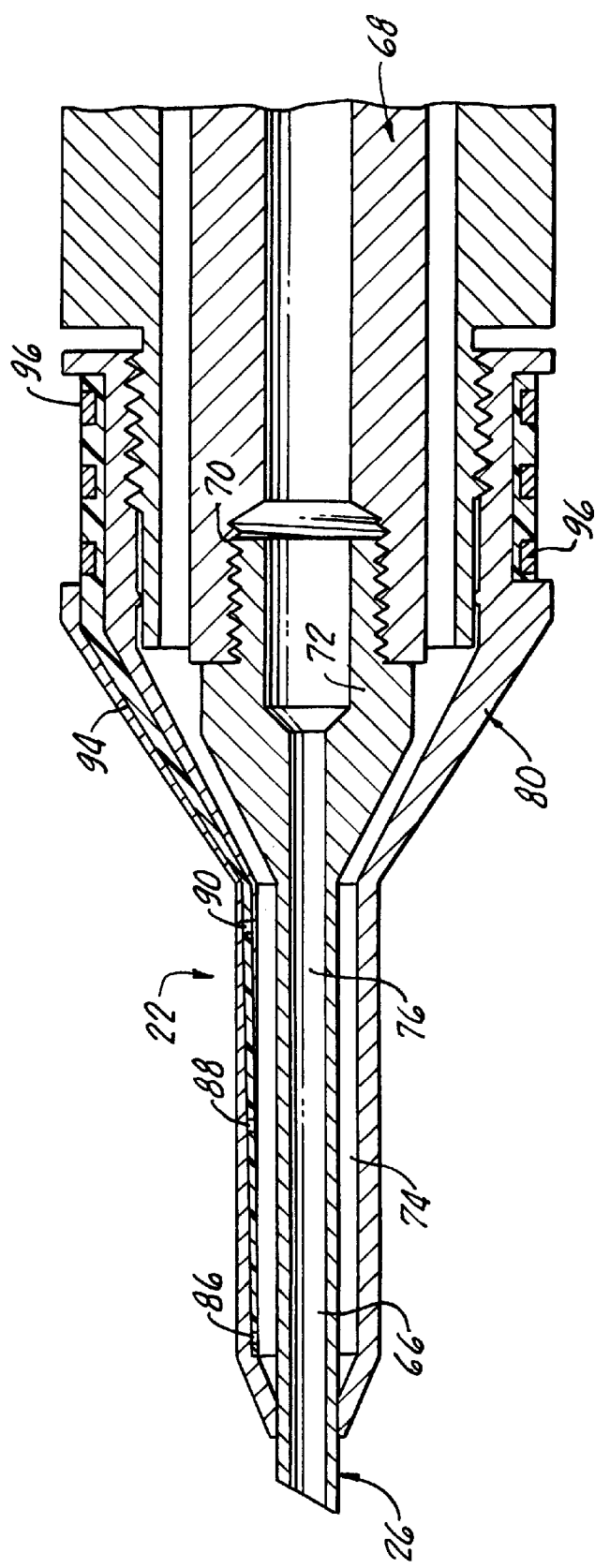
FIG. 2 shows one embodiment of the means for sensing temperature of a handpiece and needle.

With reference now to FIG. 2, there is shown the handpiece needle assembly 22 with needle 26, in cross section, which includes a metallic vibrating portion 66, which is coupled to an ultrasonic horn 68 by threads 70 formed in a base 72 of the needle 26. Lumens 74, 76, in the needle 26 provide for supply of irrigation fluid and removal or aspiration of fluid from an eye (not shown in FIG. 2) as hereinabove discussed.

Figure 3:
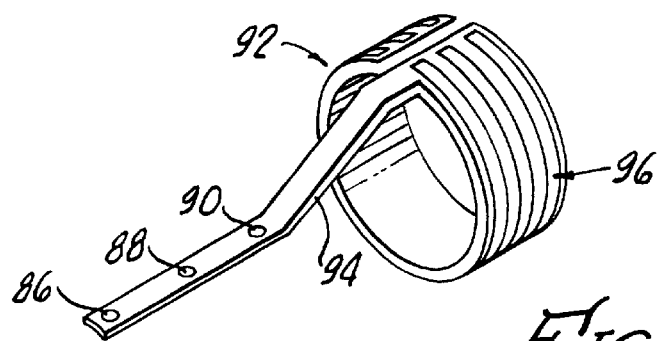
FIG. 3 is a perspective view of the sensors shown in FIG. 2 as they may be connected to a wiring harness.

An irrigation sleeve 80, preferably formed from silicon, surrounds the metallic portion 66, and includes a plurality of sensors 86, 88, 90 formed therein. Sensors are more clearly seen in FIG. 3 in which they are coupled to a harness 92, which includes electrical conduits 94, contacts 96, all molded into the irrigation sleeve 80.

Figure 4:
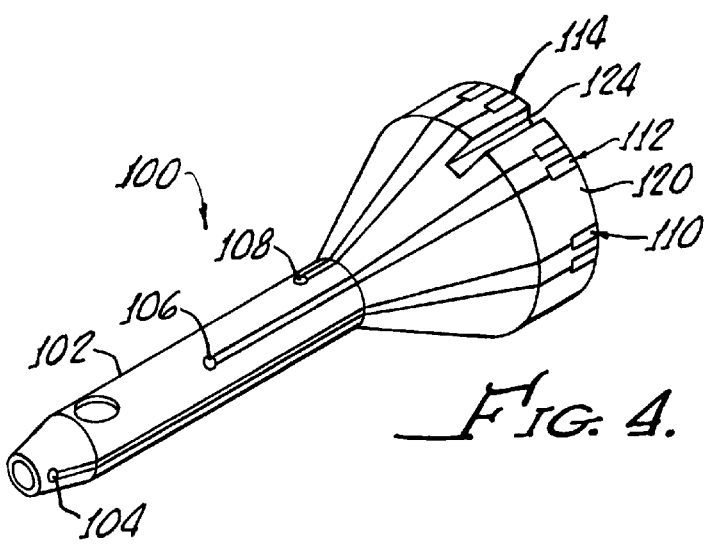
FIG. 4 is an alternative embodiment of the present invention.

With reference now to FIG. 4, there is shown an alternative needle assembly 100 showing a sleeve 102, having temperature sensors 104, 106, 108 placed therealong or embedded therein, and interconnected to corresponding contacts 110, 112, 114, disposed on a base 120 of the needle assembly 100 for sensing or measuring a temperature of a needle 122.

Figure 5:
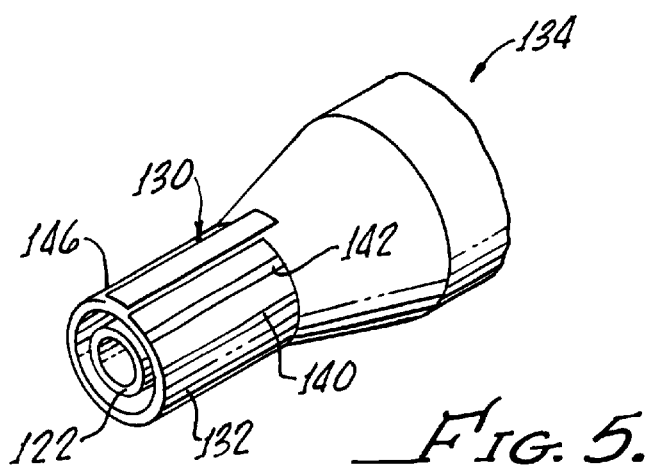
FIG. 5 shows a front portion of a handpiece body for receiving the needle shown in FIG. 4 and interconnected with the temperature sensors disposed therein.

In this embodiment, a slot 124 in the needle base 20 corresponds to a key 130 disposed on a front 132 of a handpiece body 134 as illustrated in FIG. 5. The key 130 and slot 124 provide a means for properly aligning the contacts 110, 112, 114 with mating contacts 140, 142, 146 on the front portion 132 of the handpiece 134. All of the electrical connections between the contacts and the control means 12 being made in a conventional manner.

In operation, needle temperatures of between about 70° F. and about 500° F. are within a range for controlling phaco power, irrigation fluid, and aspiration fluid rate to and from the handpiece via the control means 12. A great number of operating parameters, as is well known in the art, may be utilized to determine power and flow rates as a function of needle temperature.

Accordingly, a method in accordance with the present invention for operating a phacoemulsification system includes the steps of placing the handpiece needle 26, 122 in an operative relationship with an eye for a phacoemulsification procedure. Irrigation fluid from the irrigation fluid source 14 is provided to and through the handpiece needle 26, 122 and into the eye 50. Ultrasonic power is provided from the ultrasonic power source 26 to the handpiece needle 26, 122, for performing the phacoemulsification procedure.

A vacuum is applied from the peristaltic pump 14 which acts as a vacuum source to the handpiece needle 26, 122 for aspirating the irrigation fluid from the eye 50 through the handpiece needle 16 at a selected rate.

Importantly, the method in accordance with the present invention provides for controlling, in response to the needle temperature, one or more of the ultrasonic power being provided to the needle, the irrigation fluid being provided to the needle 26, 122, and the vacuum being applied to the handpiece needle 26, 122, for aspirating fluid from the eye 50.

Although there has been hereinabove described a phacoemulsification and method for controlling parameters such as power, irrigation fluid and vacuum to a phacoemulsification handpiece needle in accordance with the present invention for the purpose of illustrating the manner in which the invention may be used to advantage, it should be appreciated that the invention is not limited thereto. Accordingly, any and all modifications, variations or equivalent arrangement which may occur to those skilled in the art, should be considered to be within the scope of the present invention as defined in the appended claims.

What is claimed is:

1. Phacoemulsification apparatus comprising:
   a phacoemulsification handpiece having a needle and electrical means for ultrasonically vibrating said needle;
   power source means for providing electrical power to the handpiece electrical means;
   means for providing irrigation fluid to the handpiece needle and aspirating fluid from the handpiece needle;
   means for sensing a temperature of the handpiece needle; and
   control means for varying a power level provided to the handpiece electrical means from said power source means in response to the needle temperature.

2. The phacoemulsification apparatus according to claim 1 wherein said control means in response to the sensed needle temperature, varies a pulse duty cycle of the power provided to the handpiece needle by said power source means.

3. Phacoemulsification apparatus comprising:
   a phacoemulsification handpiece having a needle and electrical means for ultrasonically vibrating said needle;
   power source means for providing electrical power to the handpiece electrical means;
   means for providing irrigation fluid to the handpiece needle and aspirating fluid from the handpiece needle;
   means for sensing a temperature of the handpiece needle; and
   control means for varying an irrigation fluid rate provided to the handpiece in response to the needle temperature.

4. Phacoemulsification apparatus comprising:
   a phacoemulsification handpiece having a needle and electrical means for ultrasonically vibrating said needle;
   power source means for providing electrical power to the handpiece electrical means;

means for providing irrigation fluid to the handpiece needle and aspirating fluid from the handpiece needle;

means for sensing a temperature of the handpiece needle; and control means for varying an aspiration fluid rate from the handpiece needle in response to the needle temperature.

5. The apparatus according to claims 1, 2, 3 or 4 further comprises an irrigation sleeve surrounding the handpiece needle and the means for sensing needle temperature comprises at least one temperature sensor disposed in said irrigation sleeve.

6. The apparatus according to claim 5 wherein the means for sensing needle temperature comprises a plurality of spaced apart temperature sensors.

7. The apparatus according to claim 6 wherein each of the temperature sensors are insert molded into said irrigation sleeve.

8. The apparatus according to claim 7 further comprising harness means for interconnecting each temperature sensor to said control means.

9. A method for operating a phacoemulsification system, the system including a phacoemulsification handpiece needle, an ultrasonic power source, a vacuum source, a source of irrigating fluid, and a control unit for controlling ultrasonic power provided to the handpiece needle and the aspiration of irrigating fluid from the handpiece needle, said operating method comprising the steps of:

(a) placing the handpiece needle in an operative relationship with an eye for a phacoemulsification procedure;

(b) supplying irrigation fluid from the irrigation fluid source to and through the handpiece needle and into said eye;

(c) providing ultrasonic power from the ultrasonic power source to the handpiece needle for performing the phacoemulsification procedure;

(d) applying vacuum from the vacuum source to the handpiece needle and thereby aspirating the irrigating fluid from the eye through the handpiece needle at a selected rate;

(e) sensing a temperature of the handpiece needle; and (f) controlling, in response to the needle temperature, the ultrasonic power being provided to the handpiece needle.

10. The method according to claim 9 wherein the step of variably controlling the ultrasonic power comprises varying a pulse duty cycle of the power provided to the handpiece needle.

11. A method for operating a phacoemulsification system, the system including a phacoemulsification handpiece needle, an ultrasonic power source, a vacuum source, a source of irrigating fluid, and a control unit having a vacuum sensor for controlling ultrasonic power provided to the handpiece needle and the aspiration of irrigating fluid from the handpiece needle, said operating method comprising the steps of:

(a) placing the handpiece needle in an operative relationship with an eye for a phacoemulsification procedure;

(b) supplying irrigation fluid from the irrigation fluid source to and through the handpiece needle and into said eye;

(c) Providing ultrasonic power from the ultrasonic power source to the handpiece needle for performing the phacoemulsification procedure;

(d) applying vacuum from the vacuum source to the handpiece needle and thereby aspirating the irrigating fluid from the eye through the handpiece needle at a selected rate;

(e) sensing a temperature of the handpiece needle; and (f) controlling, in response to the needle temperature, the irrigation fluid flow being supplied to the handpiece needle.

12. A method for operating a phacoemulsification system, the system including a phacoemulsification handpiece needle, an ultrasonic power source, a vacuum source, a source of irrigating fluid, and a control unit having a vacuum sensor for controlling ultrasonic power provided to the handpiece needle and the aspiration of irrigating fluid from the handpiece needle, said operating method comprising the steps of:

(a) placing the handpiece needle in an operative relationship with an eye for a phacoemulsification procedure;

(b) supplying irrigation fluid from the irrigation fluid source to and through the handpiece needle and into said eye;

(c) providing ultrasonic power from the ultrasonic power source to the handpiece needle for performing the phacoemulsification procedure;

(d) applying vacuum from the vacuum source to the handpiece needle and thereby aspirating the irrigating fluid from the eye through the handpiece needle at a selected rate;

(e) sensing a temperature of the handpiece needle; and (f) controlling, in response to the needle temperature, the vacuum being applied to the handpiece needle.

* * * * *